United States Patent [19]

McGill

[11] 4,305,734
[45] Dec. 15, 1981

[54] RECOVERY OF HYDROCARBON COMPONENTS FROM A HYDROCARBON-CARRIER GAS MIXTURE

[75] Inventor: James C. McGill, Tulsa, Okla.
[73] Assignee: McGill Incorporated, Tulsa, Okla.
[21] Appl. No.: 76,690
[22] Filed: Sep. 19, 1979
[51] Int. Cl.³ ............................................. B01A 53/04
[52] U.S. Cl. .......................................... 55/25; 55/58; 55/62
[58] Field of Search .................. 55/25, 26, 58, 62, 68, 55/74

[56] References Cited

U.S. PATENT DOCUMENTS

| | | | |
|---|---|---|---|
| 2,354,383 | 7/1944 | Kiesskazt | 55/58 X |
| 3,225,516 | 12/1965 | Smith et al. | 55/25 |
| 3,225,518 | 12/1965 | Skrastrom et al. | 55/33 |
| 3,498,025 | 3/1970 | Bednarski | 55/33 |
| 4,056,369 | 11/1977 | Quackenbush | 55/74 X |
| 4,066,423 | 1/1978 | McGill et al. | 55/58 X |
| 4,129,424 | 12/1978 | Armond | 55/62 X |
| 4,144,037 | 3/1979 | Armond et al. | 55/62 X |
| 4,153,428 | 5/1979 | Saunders et al. | 55/62 X |

FOREIGN PATENT DOCUMENTS

| | | |
|---|---|---|
| 845312 | 8/1960 | United Kingdom . |
| 1421786 | 1/1976 | United Kingdom . |
| 1437344 | 5/1976 | United Kingdom . |
| 1437600 | 5/1976 | United Kingdom . |
| 1456465 | 12/1976 | United Kingdom . |

Primary Examiner—John Adee
Attorney, Agent, or Firm—Dunlap, Codding & McCarthy

[57] ABSTRACT

An improved process for recovering hydrocarbon components from a hydrocarbon-carrier gas mixture wherein the mixture is passed through a solid adsorbent bed capable of selectively adsorbing the hydrocarbon and passing substantially hydrocarbon-free carrier gas. The hydrocarbon components are recovered by passing a hydrocarbon-rich flushing gas mixture through the adsorbent bed followed by subjecting the adsorbent bed to a change in pressure to desorb the hydrocarbon components and produce a hydrocarbon-rich product stream. Further hydrocarbon enrichment may be obtained by passing the product stream to another solid adsorbent bed to adsorb the hydrocarbon and pass further substantially hydrocarbon-free carrier gas. The hydrocarbon components are then recovered by subjecting the other adsorbent bed to a vacuum to desorb the hydrocarbon and produce a richer hydrocarbon product stream.

51 Claims, 3 Drawing Figures

RECOVERY OF HYDROCARBON COMPONENTS FROM A HYDROCARBON-CARRIER GAS MIXTURE

BACKGROUND OF THE INVENTION

1. Field of the Invention

The present invention relates generally to the field of hydrocarbon removal from hydrocarbon-carrier gas mixtures, and more particularly but not by way of limitation, to processes for the economical removal of hydrocarbon components from hydrocarbon-air mixtures and the enrichment of hydrocarbon product streams produced thereby for use as fuel or chemical feed stock.

2. Discussion

Many industrial operations have losses of hydrocarbon gases to the atmosphere. This venting represents valuable product losses as well as presenting serious contamination to the ambient atmosphere.

Should the vented hydrocarbon components be mixed with air, the possibility of ignition and resulting explosions is a very serious possibility. For example, mixtures of methane and air in which the methane concentration varies from about 4% by volume to about 14% by volume will explode if ignited. As a result of this explosion hazard, many hydrocarbon bearing streams are vented directly to the atmosphere rather than attempting to process the vapor stream for fear of ignition and resulting explosions.

A typical example is the loss of methane from coal mines. The methane exists in certain types of coal mines and is produced through drilled wells much as natural gas is produced through wells. These wells are drilled into the coal seams and the methane is extracted by application of vacuum to prevent the methane from flowing back into the coal mine where its presence would present a hazard to the workers of the mine. The methane content of the extracted gas from these wells, sometimes referred to as bore holes, may begin at nearly 100% by volume methane and reduce to less than 30% by volume methane as the mine is worked. The reason for this is that more air is drawn from the bore holes as the coal mine matures. This gas is used as fuel to power mining machines and it becomes difficult to use the gas as lean concentrations of methane are obtained.

Another coal mine operation in which methane is lost is through ventilation systems. A design of a typical ventilation system is that in which air is circulated through the operating coal mine in sufficient volume that the methane content of the air leaving the coal mine is frequently less than 1% by volume, which is below the lower flammability limit of approximately 4% by volume methane in air mentioned above. Even so, this can represent a significant loss of potential fuel, and depending upon regulatory conditions, the methane loss may represent serious contamination.

SUMMARY OF THE INVENTION

The present invention provides a process whereby the methane vented from industrial operations such as coal mines may be economically and safely recovered for utilization as a fuel. The invention provides a process for recovering hydrocarbon components from a hydrocarbon-carrier gas mixture in which the mixture is passed through an adsorber containing an adsorbent bed of material capable of selectively adsorbing the hydrocarbon components from the mixture to produce a first venting stream of substantially hydrocarbon-free carrier gas; venting the first venting stream; terminating the flow of the inlet stream to the adsorber; flushing the adsorbent bed of the adsorber with a flushing stream of gas comprising a mixture rich in the adsorbed hydrocarbon components; venting the flushing stream; and lowering the pressure of the hydrocarbon laden adsorbent bed of the adsorber to desorb hydrocarbon components therefrom and producing thereby a product stream comprising a gas mixture rich in the adsorbed hydrocarbon components.

Further enrichment of the hydrocarbon bearing product stream may be obtained by passing the product stream through another adsorber containing an adsorbent bed of material capable of selectively adsorbing the hydrocarbon components from the product stream to produce a second venting stream of substantially hydrocarbon-free carrier gas; venting the second venting stream; terminating the flow of the product stream to the other adsorber; flushing the adsorbent bed of the adsorber with a flushing stream of gas comprising a mixture rich in the adsorbed hydrocarbon components; venting the flushing stream; and lowering the pressure of the hydrocarbon laden absorbent bed of the other adsorber to desorb the hydrocarbon components therefrom and producing thereby a second product stream comprising a gas mixture richer in the adsorbed hydrocarbon components.

An object of the present invention is to provide a process for the recovery of hydrocarbon components from a hydrocarbon-carrier gas mixture while producing a hydrocarbon rich product stream which is useable as a fuel or feed to a chemical process.

Another object of the present invention, while achieving the above stated object, is to provide a process for the recovery and enrichment of hydrocarbon fuel from mixtures of hydrocarbon and carrier gases over a wide variation of concentrations.

Another object of the present invention, while achieving the above stated objects, is to provide a process for the safe and economical recovery and enrichment of hydrocarbon components from hydrocarbon-carrier gas mixtures.

Other objects, features and advantages of the present invention will become clear when the following description is read in conjunction with the accompanying drawings and appended claims.

DESCRIPTION

The discussion herein will be directed to the recovery of hydrocarbon components from hydrocarbon-carrier gas mixtures in general, and more specifically, to the recovery of methane from methane-air streams such as found in many industrial operations. An example of such an industrial operation is a coal mine, as the application of the present invention to methane production from coal mining operations is of major concern to the welfare of the United States at this time, and to many other countries of the world in which coal mining is a major industry or in which the escape of methane from coal mines presents a possible air pollution hazard, and certainly, the loss of a valuable resource. While methane-air mixtures are of prime concern, another typical example is the separation of ethylene from air or nitrogen streams which vent from polyethyene manufacturing facilities; yet another example is the separation of methane from other gases produced during coal gasification; and in the recovering of methane from land-fill operations, and the enrichment of low Btu natural gas.

Figure 1:
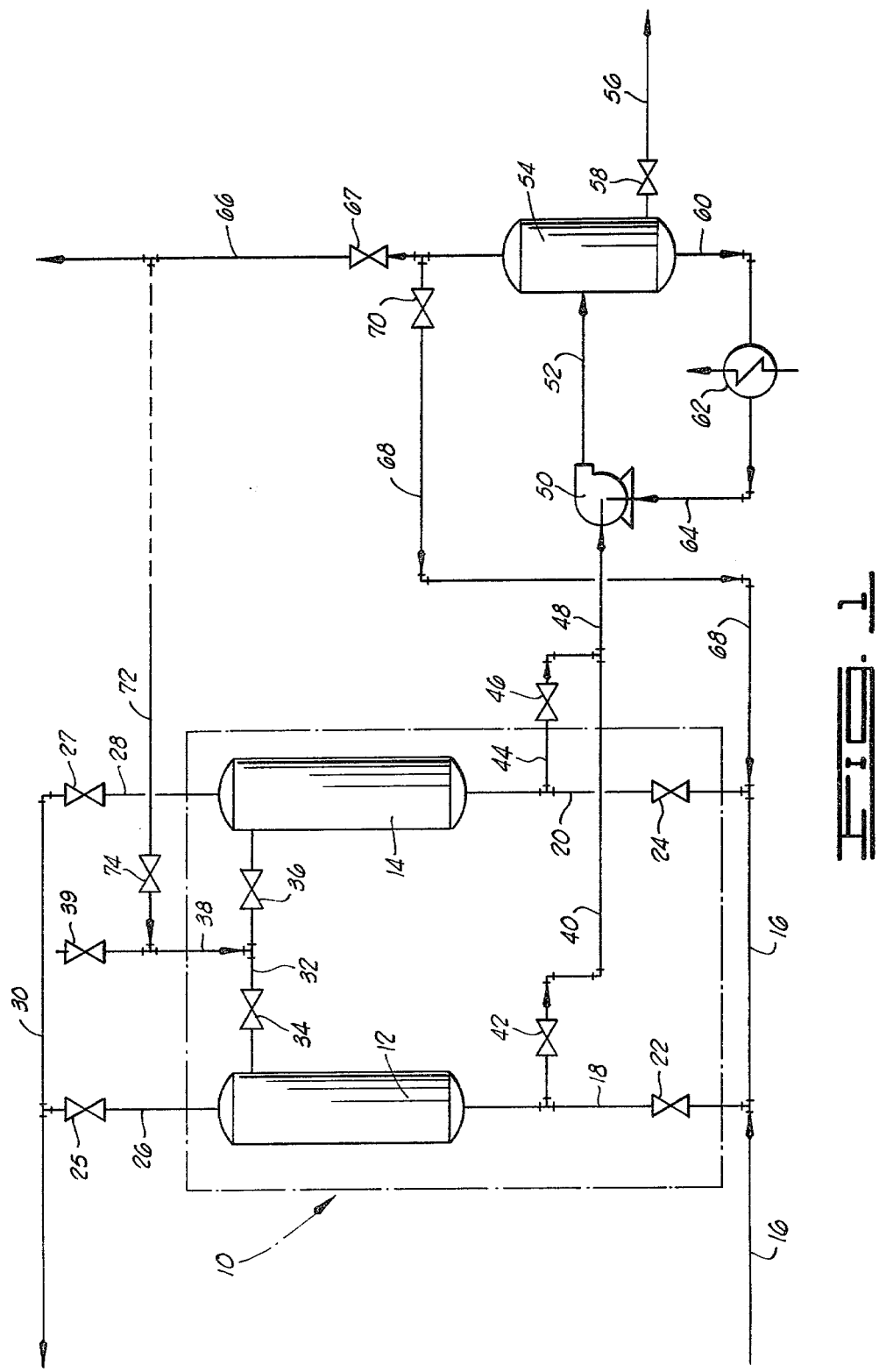
FIG. 1 is a flow diagram showing a preferred embodiment of the present invention.

Referring to the drawings in general and with specific reference to FIG. 1, shown therein is a diagram of a process flow layout construction to practice the present invention. A first adsorber battery, depicted by the broken line box 10, comprises a first adsorber vessel 12 and a second adsorber vessel 14, each of the adsorber vessels 12, 14 containing a bed of solid adsorbent material capable of selectively adsorbing the hydrocarbon components of a hydrocarbon-carrier gas mixture. The adsorbers 12, 14 are of standard design, and the adsorber material is typically activated carbon. It will be appreciated that although activated carbon is used in the present example, other solid adsorbents may be effectively employed in the process and apparatus of this invention. The adsorbers 12, 14 are each provided with internal adsorbent support baffles or plates, gas flow directing baffles, and high pressure relief valves, as well as pressure and temperature indicating gauges conventionally employed with solid adsorbent devices; however, for the sake of simplifying the process layout depicted in FIG. 1, these details are not shown.

As will become clear with the description that follows, the first and second adsorbers 12 and 14 serve as parallel adsorbers which are alternately connected to a source of high pressure inlet feed gas. While one bed is at high pressure, the other bed will be flushed and placed on low pressure vacuum in a manner described below.

A feed conduit 16 is connected to a pressurized source of hydrocarbon-carrier gas mixture, such as methane-air, and is connected to a first inlet conduit 18 and an inlet conduit 20 leading, respectively, to the first and second adsorbers 12 and 14. Valves 22 and 24 are provided in the first and second inlet conduits 18 and 20, respectively.

A first outlet conduit 26 and a second outlet conduit 28 are provided as exhaust lines for the first and second adsorbers 12, 14, respectively. The outlet conduits 26, 28 have valves 25 and 27 disposed therein, respectively, and connect to a carrier gas outlet conduit 30 which leads to a venting discharge area such as to an atmosphere discharge point, for example.

The first and second adsorbers 12, 14 are interconnected with a flushing conduit 32 near the top portions thereof having a pair of valves 34 and 36 disposed therein, and a flushing conduit 38, having a valve 39, is connected to the flushing conduit 32 between the valves 34 and 36; the flushing conduit 38 is open to the atmosphere at its distal end when the valve 39 is opened.

A vacuum conduit 40, having a valve 42 disposed therein, communicates with the first adsorber 12 by connecting to the first inlet conduit 18 downstream of valve 22, and a vacuum conduit 44, having a valve 46 disposed therein, communicates with the second adsorber vessel 14 by connecting to the second inlet conduit 20 downstream of the valve 24. The vacuum conduits 40 and 44 are connected to a conduit 48 which is connected to the suction port of a vacuum pump 50, and the pump discharge port is connected to a discharge conduit 52 which connects near the midsection to a separator vessel 54.

Preferably, the vacuum pump 50 is a liquid ring vacuum pump capable of producing a near vacuum in either adsorbent bed during regeneration of the adsorbers. The use of a liquid ring pump is advocated to minimize the risk of explosion, and also because this type of vacuum pump is highly efficient in the present use. These pumps are available, for example, from Nash Engineering, Norwalk, Connecticut, and because such pumps are conventional, a detailed description of same need not be provided herein.

The separator 54 is a vessel operated slightly above atmospheric pressure and is designed to separate the vapor and liquid components of the pump effluent and to further separate the immiscible liquid used by the liquid ring pump from any recovered hydrocarbon liquid condensed by the inherent cooling action of the liquid ring vacuum pump 50 if condensible hydrocarbon components are contained in the inlet stream of hydrocarbon-carrier gas mixture entering the feed conduit 16. If such condensible hydrocarbon components are liquefied in the separator 54, these liquid hydrocarbon components are withdrawn from the separator via a liquid outlet conduit 56 having a valve 58. In many applications, such as in the utilization of the present invention for the recovery of methane from a methane-air mixture, liquid condensibles are usually not present and the valve 58 will remain closed. On the other hand, when experiencing the inlet of constituents such as butanes and higher molecular weight hydrocarbons, it will be necessary to periodically withdraw such liquid condensibles via the conduit 56. The heavier pumping liquid, typically water, trapped in the separator 54 is withdrawn therefrom via the bottom discharge conduit 60. Antifreeze may also be used as the pumping liquid in the liquid ring pump 50 where freezing ambient temperatures are experienced. The bottom discharge conduit 60 is connected to a cooler 62, which is an indirect heat exchanger that may employ any suitable cooling medium for cooling the liquid flowing through the bottom discharge conduit 60. The cooled liquid passing to the cooler 62 via the discharge conduit 60 is passed to the conduit 64 which connects the cooler 62 and the liquid suction port of the liquid ring vacuum pump 50.

Connected to the top of the separator 54 is a product discharge conduit 66 which has a valve 67 disposed therein. A recycle conduit 68, having a valve 70 disposed therein, is connected to the discharge conduit 66 and has its distal end connected to the feed conduit 16. A product flushing conduit 72, having a valve 74 disposed therein, may interconnect with the product discharge conduit 66, at a point downstream of the valve 67, and with the flushing conduit 38 at a point downstream of the valve 39, or the product flushing conduit 72 may be connected to a source of hydrocarbon gas, such as methane.

Having described the equipment depicted in the flow layout of FIG. 1, the discussion will now turn to an operative example. An inlet of hydrocarbon-carrier gas mixture is admitted to the first adsorber battery 10 via the feed conduit 16 with the following valve settings: valves 22 and 25 in the first inlet conduit 18 and the first outlet conduit 26, respectively, are open; valves 24 and 27 in the second inlet conduit 20 and the second outlet conduit 28, respectively, are closed; the valve 42 in the vacuum conduit 40 is closed; the valve 34 in the backflush conduit 32 is closed; and all the other valves shown in FIG. 1 will be considered closed until specifically mentioned otherwise hereinbelow.

The inlet stream passes through the feed conduit 16 and the first inlet conduit 18 to the first adsorber 12, which for the purpose of the discussion will be considered the operative or processing adsorber of the first adsorber battery 10. As the inlet stream is passed in contact with the adsorbent bed of the first adsorber 12, the hydrocarbon components from the inlet stream are adsorbed to produce a first venting stream of substantially hydrocarbon free carrier gas which passes from the first adsorber 12 via the first outlet conduit 26 to the carrier gas outlet conduit 30 where the stripped carrier gas is passed to a remote discharge point. In the case of a methane-air inlet stream, the methane is adsorbed onto the surface of the carbon to a greater degree than is the nitrogen and oxygen present in the air, and the air leaving the carbon adsorption system of the first adsorber 12 may contain less than 1% by volume methane, depending upon the size of the first adsorber 12 and the flow rate of the inlet stream, and in this case, the stripped air may be vented directly to the atmosphere safely and with the conservation of the natural resource. The adsorption takes place safely because no source of ignition exists in the first adsorber 12. During the above operation, the second activated carbon adsorber, the second adsorber 14, has been isolated from the first adsorber 12; it is recommended that one of the carbon adsorbers be actively in the adsorption mode, while the second adsorber is in the desorbing mode at all times, and these modes will alternate between the first and second adsorbers 12, 14.

When, by conventional indicators, it has been determined that the first adsorber 12 has adsorbed sufficient hydrocarbon components from the inlet stream to require regeneration, the regeneration cycle will be performed in the following manner. It is assumed for the purpose of this discussion that the second adsorber 14 has been regenerated and is in the stand-by mode awaiting to be placed in the onstream or adsorbing mode. At this time, the valves 24 and 27 disposed in the second inlet conduit 20 and the second outlet conduit 28, respectively, are opened, and simultaneously, the valves 22 and 25 disposed in the first inlet conduit 18 and in the first outlet conduit 26, respectively, are closed; this effects the routing of the inlet stream of hydrocarbon-carrier gas mixture to the second adsorber 14 via the second inlet conduit 20. In like manner to that described for the passage of the inlet stream through the first adsorber 12, the inlet stream will pass through the second adsorber 14, being substantially stripped of its hydrocarbon content and producing the first venting stream of substantially hydrocarbon free carrier gas which is vented from the second adsorber 14 via the second outlet conduit 28 to the carrier gas outlet conduit 30.

Once the first adsorber 12 has been taken off-stream and isolated from the inlet stream of hydrocarbon-carrier gas, it is ready for regeneration as follows. At this point in time, the adsorbent material contained in the first adsorber 12 starts its regeneration cycle with a large volume of carrier gas rich vapor in the void space between the carbon particles of the bed. If this carrier gas (which will be air in the case of an inlet stream of methane-air mixture) is not removed prior to regeneration, the carrier gas will tend to dilute the hydrocarbon product and produce a hydrocarbon product of approximately 50% by volume, when the feed gas in conduit 16 is 30% methane by volume. Enrichment of the product stream is accomplished by flushing the offstream first adsorber 12 with flushing gas as the pressure on the adsorbent bed of the first adsorber 12 is first lowered, the flushing gas being selected as one which will be adsorbed to a greater degree than the carrier gas so that the carrier gas is displaced from the adsorbent bed to produce a displaced carrier gas stream. For example, a stream of gas which is substantially richer in hydrocarbon than the feed gas is passed through the first adsorber 12 via the flushing conduit 72, the flushing conduit 38 and the flushing conduit 32 by opening the valves 74 and 34. As indicated above, the flushing conduit 72 may be connected to the product discharge conduit 66 during continuous operation of the process of FIG. 1, or the flushing conduit 72 may be connected to a source of substantially pure hydrocarbon gas. In either case, the flushing gas is connected to the first adsorber 12, the valve 42 is opened, and the liquid ring vacuum pump 50 is actuated to commence the lowering of pressure on the first adsorber 12. As this is undertaken, the displaced carrier gas is pushed out of the void spaces between the adsorbent particles as it is displaced by the substantially pure hydrocarbon flushing gas. During this early period of pressure reduction on the first adsorber 12, the displaced carrier gas (which will be air in the case of a methane-air inlet stream) is removed from the first adsorber 12 and is passed via the liquid ring vacuum pump 50 into the separator 54 where it is vented via the product discharge conduit 66. During this early period of flushing, the displaced carrier gas is recycled via the recycle conduit 68, by closing the valve 67 and opening the valve 70, back to the feed conduit 16 to pass through the on-stream second adsorber 14. After a short period of time, the hydrocarbon flushing and the recycled displaced carrier gas are shut off by closing valves 34 and 74 in the flushing conduits 32 and 72, respectively; closing valve 70 in the recycle conduit 68; and opening valve 67 in the product discharge conduit 66. The regeneration then proceeds as follows.

The opening of valve 42 of the vacuum conduit 40 and the actuation of the liquid ring vacuum pump 50 will reduce the pressure on the activated carbon material in the first adsorber 12 to a vacuum of between about 1 inch of mercury absolute and about 5 inches of mercury absolute. Of course, the greatest efficiency of desorption is at the lower pressure, and the lowest efficiency of desorption will occur at the higher mentioned vacuum pressure. The liquid ring vacuum pump employs a water motive force and has no metal-to-metal contact parts. As a result, high vacuums can be obtained safely. The lowering of the pressure on the hydrocarbon laden adsorbent bed of the first adsorber 12 causes the removal of the hydrocarbon components therefrom and produces thereby a first product stream that flows through the vacuum conduits 40, 48, through the vacuum pump 50, through the discharge conduit 52 and to the separator 54 where the hydrocarbon components are separated from the liquid injected into the first product stream by the liquid ring vacuum pump 50. For example, in the case of a methane-air mixture, the methane and the water are separated in the separator 54, and the water is recycled to the liquid ring vacuum pump 50 via the bottom discharge conduit 60, and after being cooled in the cooler 62, the water is returned to the liquid ring vacuum pump 50 via the conduit 64. The first product stream, having substantially lost its water content in the separator 54, is passed via the overhead product discharge conduit 66 to facilities which can consume it as a fuel.

After the vacuum in the first adsorber 12 is reduced to a volume of approximately one inch of mercury absolute, a stripping gas, in this case air, may be introduced over the top of the activated carbon. That is, valve 39 in the flushing conduit 38 is opened, along with valve 34 in the flushing conduit 32, and air is admitted to the adsorbent bed in the first adsorber 12 as the liquid ring vacuum pump 50 continues to pull a vacuum on the first adsorber 12. This serves to strip the last remaining traces of hydrocarbon from the adsorbent bed, and it further tends to remove any heavy hydrocarbon compounds which may have accumulated on the adsorbent bed by the introduction of same with the inlet hydrocarbon-carrier gas mixture. It has been found that without the air purge being used, the adsorbent bed may eventually be deactivated by accumulation of heavy hydrocarbon components. However, when heavy hydrocarbons do not exist to a significant degree, the air purge may be eliminated. Air is admitted only briefly to the first adsorbent bed 12, and the air admission is shut off by closing the valves 34 and 39. This momentary intrusion of air into the system will normally have a non-consequential effect on the product stream flowing through the product discharge conduit 66. If objectionable, the air purge can be removed by simultaneously closing valve 67 and opening valve 70 to recycle the air purge via the recycle conduit 68 in the manner described above for the flushing hydrocarbon stream.

When, by conventional indicators, it has been determined that the second adsorber 14 has adsorbed sufficient hydrocarbon components from the inlet stream to require regeneration, the regeneration cycle for the second adsorber 14 will be conducted in the manner described above for the regeneration cycle of the first adsorber 12. While the second adsorber 14 has been on-stream, the first adsorber 12 will have been regenerated and will be standing by awaiting to be placed in the on-stream or adsorbing mode. At the end of the regeneration cycle for the first adsorber 12, the valve 42 will be closed and the liquid ring vacuum pump 50 will be deactivated. The second adsorber 14 will be taken off-stream by closing valves 24 and 27 disposed in the second inlet conduit 20 and the second outlet conduit 28, respectively, and simultaneously, the first adsorber 12 will be put on-stream by opening the valves 22 and 25 disposed in the first inlet conduit 18 and in the first outlet conduit 26, respectively. This routes the inlet stream of hydrocarbon-carrier gas mixture entering the feed conduit 16 to the first adsorber 12 via the first inlet conduit 18.

Regeneration of the second adsorber 14 is commenced with the hydrocarbon flushing effected by opening valves 74 and 36 disposed in the product flushing conduit 72 and the flushing conduit 32, respectively, while opening valve 46 in the vacuum conduit 44 and actuating the liquid ring vacuum pump 50. With the exception that the aforestated apparatus are involved instead of that associated with the first adsorber 12, the regeneration, including the flushing by a substantially pure hydrocarbon product, continues for the second adsorber 14 in the identical manner described above for the regeneration cycle of the first adsorber 12. Since the regeneration cycle will take less time than the time required to bring the on-stream adsorber to saturation, there will always be an off-stream adsorber waiting to be placed on-stream at the end of the process run for the onstream adsorber. In this way, the first and second adsorbers 12, 14 of the first adsorber battery 10 alternate on-stream time.

In typical runs with a 40% by volume methane in an inlet stream of methane-air mixture, a methane product of 95% by volume methane in the first product stream can be produced. Tests have demonstrated that using 10% by volume methane in an inlet stream of methane-air mixture can be enriched up to about 90% by volume of methane in the first product stream. For example, a single bed utilizing two runs which were different only in the step of flushing the beds during the regeneration cycle produced the following results. First, a bed of activated carbon was loaded to saturation utilizing 10% by volume of methane in an inlet stream of methane-air mixture. Following the loading period, the bed was regenerated using a liquid ring vacuum pump, and the maximum purity of the first product stream leaving the separator was 42% by volume methane in the first product stream. Immediately following, the same bed of activated carbon was loaded with the 10% by volume methane of the inlet stream of methane-air mixture, and following loading to saturation, the bed was flushed with pure methane for two and one-half minutes at the commencement of the vacuum cycle. Following this, the flushing of methane was terminated, and the vacuum was continued to desorb the activated carbon. A maximum and generally constant 78% by volume methane was obtained as the first product stream.

Figure 2:
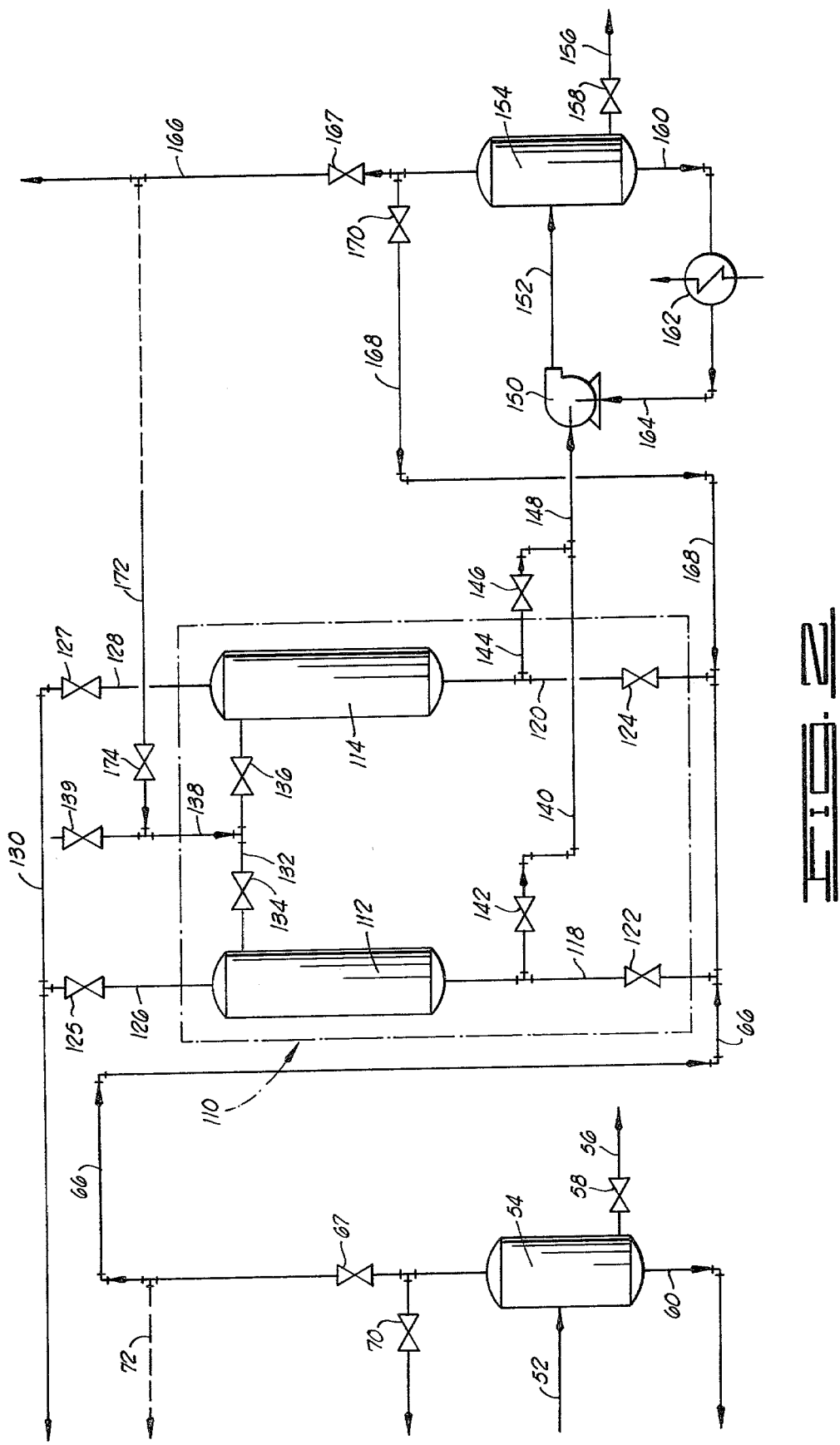
FIG. 2 is a flow diagram showing a modification of the process depicted in FIG. 1.

FIG. 2 represents a variation of the present invention in which very lean stream of hydrocarbon may be separated from a carrier gas, such as methane from air in ventilation systems as discussed hereinabove. This can also occur at the end of production of methane from bore holes in coal mining. The process of FIG. 2 will be involved where the regenerated stream of hydrocarbon (the first product stream exhausted from the product discharge conduit 66) is not sufficiently rich to be used directly in fuel consuming equipment. In a typical example, an inlet stream of 1% methane-99% air by volume would produce a methane product of approximately 10% by volume methane in the process depicted in FIG. 1. This methane product would simply be too lean to be used sufficiently in fuel consuming equipment, and the enrichment of such a stream is undertaken by the adaptation of the process depicted in FIG. 2.

The process depicted in FIG. 2 is a continuation of that which has been described in FIG. 1. That is, it is anticipated that the first product stream flowing through the product discharge conduit 66 will be fed to the process equipment of FIG. 2 when the hydrocarbon content of the first product stream is insufficient.

In FIG. 2, there is shown a diagram of a process flow layout constructed to be utilized in tandem with that shown in FIG. 1 to practice the present invention. A second adsorber battery 110 is provided which comprises a first adsorber vessel 112 and a second adsorber vessel 114, each of the adsorber vessels 112, 114 containing a bed of solid adsorbent material capable of selectively adsorbing the hydrocarbon components of a hydrocarbon-carrier gas mixture. In practice, the adsorbers 112 and 114 are identical in construction and detail to that described above for the adsorbers 12 and 14 of the first adsorber battery 10.

In like manner to that of the first adsorber battery 10, the first and second adsorbers 112, 114 of the second adsorber battery 110 serve as parallel adsorbers which are alternately connected to receive the first product stream exiting the separator 54 via the product discharge conduit 66. While one bed will be on-stream, the other bed will be backwashed and placed on low pressure vacuum in the manner described above.

The product discharge conduit 66 is connected to a first inlet conduit 118 and an inlet conduit 120 leading, respectively, to the first and second adsorbers 112 and 114. Valves 122 and 124 are provided in the first and second inlet conduits 118 and 120. A first outlet conduit 126 and a second outlet conduit 128 are provided as exhaust lines for the first and second adsorbers 112, 114, respectively. The outlet conduits 126, 128 have valves 125 and 127 disposed therein, respectively, and connect to a carrier gas outlet conduit 130 which leads to a venting discharge area such as to an atmospheric discharge point, in the same manner as that described above for the carrier gas outlet conduit 30.

The first and second adsorbers 112, 114 are interconnected with a flushing conduit 132 near the top portion thereof having a pair of valves 134 and 136 disposed therein, and a flushing conduit 138, having a valve 139, is connected to the flushing conduit 132 between the valves 134 and 136; the flushing conduit 138 is opened to the atmosphere at its distal end when the valve 139 is opened.

A vacuum conduit 140, having a valve 142 disposed therein, communicates with the first adsorber 112 by connecting to the first inlet conduit 118 downstream of valve 122, and a vacuum conduit 144, having a valve 146 disposed therein, communicates with the second adsorber vessel 114 by connecting to the second inlet conduit 120 downstream of the valve 124. The vacuum conduits 140 and 144 are connected to a conduit 148 which is connected to the suction port of a vacuum pump 150, and the pump discharge port is connected to a discharge conduit 152 which connects near the midsection to a separator vessel 54. Preferably, the vacuum pump 150 is a liquid ring vacuum pump of the type described above for the vacuum pump 50. In fact, it is possible in some applications, through appropriate manifold valving, to have a common liquid ring vacuum pump serving both the first and second adsorber batteries 10 and 110.

As described above for the separator 54, the separator 154 is a vessel which operates slightly above atmospheric pressure and is designed to separate the vapor and liquid components of the pump effluent. It is unlikely that condensable hydrocarbon components will be liquefied in the separator 154 since these should have been removed in the previous separator 54. Accordingly, it is not anticipated that it would be necessary to have a bottom blow-off for the separator 154; however, a bottom blow-off conduit 156 and valve 158 are shown.

The heavier pumping liquid, typically water, trapped in the separator 154 is withdrawn therefrom via the bottom discharge conduit 160. Antifreeze may also be used as the pumping liquid in the liquid ring pump 150 where freezing ambient temperatures are experienced. The bottom discharge conduit 160 is connected to a cooler 162, which is like the indirect heat exchanger 62 described above. The cooled liquid passing through the cooler 162 discharges via a conduit 164 and is fed to the liquid suction port of the liquid ring vacuum pump 150.

Connected to the top of the separator 154 is a product discharge conduit 166 which has a valve 167 disposed therein. A recycle conduit 168, having a valve 170 disposed therein, is connected to the discharge conduit 166 and has its distal end connected to the product discharge conduit 66. A product flushing conduit 172, having a valve 174 disposed therein, may interconnect with the product discharge conduit 166, at a point upstream of the valve 167, and with the flushing conduit 138 at a point downstream of the valve 139, or the product flushing conduit 172 may be connected to a source of a hydrocarbon rich gas, such as methane.

With the above description of the equipment depicted in the flow layout of FIG. 2, the discussion will now turn to an operative example of the flow of the process layout of FIG. 2 in tandem with the flow layout of FIG. 1. The first product stream is discharged from the separator 54 via the product discharge conduit 66 and is admitted to the second adsorber battery 110 via the following valve settings: valves 122 and 125 in the first inlet conduit 118 and the first outlet conduit 126, respectively, are open; valves 124 and 127 in the second inlet conduit 120 and the second outlet conduit 128, respectively, are closed; the valve 142 in the vacuum conduit 140 is closed; the valve 134 in the flushing conduit 132 is closed; and all the other valves shown in FIG. 2 downstream of the valve 67 in the product discharge conduit 66 will be considered closed until specifically mentioned otherwise hereinbelow.

The first product stream passes through the product discharge conduit 66, entering the first adsorber 112 via the first inlet conduit 118 where the hydrocarbon content is adsorbed until the loading saturation of the adsorbent bed of the first adsorber 112. Hydrocarbon removal from the first product stream produces a second venting stream of substantially hydrocarbon free carrier gas which passes from the first adsorber 112 via the first outlet conduit 126 to the carrier gas outlet conduit 130 where the stripped carrier gas is passed to a remote discharge point. In case of a methane-air inlet stream, the methane should be adsorbed by the adsorbent in the first adsorber 112 such that the air leaving the first adsorber 112 may contain less than 1% by volume methane, depending upon the size of the first adsorber 112 and the flow rate of the first product stream. During this operation, the second activated carbon adsorber 114 has been isolated from the first adsorber 112, and in like manner described above, it is recommended that one of the carbon adsorbers be actively in the adsorbtion mode, while the second adsorber is in the desorbing mode at all times, and these modes will alternate between the first and second adsorbers 112, 114.

When the first adsorber 112 has been loaded, the regeneration cycle will be performed in the following manner. Assuming that the second adsorber 114 has previously been regenerated and is in the standby mode awaiting replaced onstream, the valves 124 and 127 disposed in the second inlet conduit 120 and the second outlet conduit 128, respectively, are closed, and simultaneously, the valves 122 and 125 disposed in the first inlet conduit 118 and in the first outlet conduit 126, respectively, are closed. This routes the first product stream to the second adsorber 114 via the second inlet conduit 120. In like manner to that described for the passage of the first product stream through the first adsorber 112, the first product stream will pass through the second adsorber 114, being substantially stripped of its hydrocarbon content and producing the second venting stream of substantially hydrocarbon-free carrier gas which is vented from the adsorber 114 via the second outlet conduit 128 to the carrier gas outlet conduit 130.

Once the first adsorber 112 has been taken off stream and isolated from the inlet stream of hydrocarbon carrier gas, it is ready for regeneration as follows. At this point in time, the first adsorber 112 starts at the regeneration cycle with a large volume of carrier gas rich vapor in the void space between the carbon particles of the bed. In like manner to that described above, enrichment of the product is accomplished by flushing the first adsorber 112 with a flushing gas prior to lowering the pressure on the first adsorber 112, the flushing gas being one which will be adsorbed to a greater degree than the carrier gas so that the carrier gas is displaced from the adsorbent bed to produce a displaced carrier gas stream which is vented. In the example at hand, a hydrocarbon gas is passed through the first adsorber 112 via the flushing conduit 172, the flushing conduit 138 and the flushing conduit 136 by opening the valves 174 and 134. As indicated above, the flushing conduit 172 may be connected to the product discharge conduit 166 during continuous operation of the process of FIGS. 1 and 2, or the flushing conduit 172 may be connected to a source of hydrocarbon rich gas. As described in FIG. 1, the flushing gas is connected to the first adsorber 112, the valve 142 is opened, and the liquid ring vacuum pump 150 is actuated to commence the lowering of pressure on the second adsorber 112. As this is undertaken, the carrier gas is displaced from the void spaces between the adsorbent particles by the hydrocarbon rich flushing gas. During this early period of pressure reduction on the first adsorber 112, the carrier gas is removed from the first adsorber 112 and is passed via the liquid ring vacuum pump 150 into the separator 154 where it is vented via the product discharge conduit 166. During this early period of flushing the carrier gas is recycled via the recycle conduit 168 (by closing the valve 167 and opening the valve 170) back to the product discharge conduit 66 to pass through the on-stream second adsorber 114. After a short period of time, the hydrocarbon flushing and the recycled carrier gas are shut off by closing valves 134 and 174 in the flushing conduits 132 and 172, respectively; closing valve 170 in the recycle conduit 168; and opening valve 167 in the product discharge conduit 166. The regeneration then proceeds as follows.

The opening of the valve 142 of the vacuum conduit 140 and the actuation of the liquid ring vacuum pump 150 will reduce the pressure on the activated carbon material in the first adsorber 112 to between about 1 and 5 inches of mercury absolute. This causes the removal of the hydrocarbon components therefrom and produces thereby a second product stream that flows through the vacuum conduits 140, 148, through the vacuum pump 150, through the discharge conduit 152 and to the separator 154 where the hydrocarbon components are separated from the liquid injected into the second product stream by the liquid ring vacuum pump 150. In the case of a methane-air mixture, the methane and the water are separated in the separator 154, and the water is removed via the bottom discharge conduit 160; after being cooled in the cooler 162, the water is returned to the liquid ring vacuum pump 150 via the conduit 164. The enriched second product stream, having substantially lost its water content in the separator 154, is passed via the overhead product discharge conduit 166 to facilities which can consume it as a fuel.

After the vacuum in the first adsorber 112 is reduced to a volume of approximately one inch of mercury absolute, an air purge is introduced over the top of the activated carbon. That is, valve 139 in the flushing conduit 138 is opened along with valve 134 and the flushing conduit 32 and air is admitted to the adsorbent bed in the first adsorber 112 as the liquid ring vacuum pump 150 continues to pull a vacuum on the first adsorber 112. This air purge serves as a stripping gas to remove the last remaining traces of hydrocarbon from the adsorbent bed, and as discussed above, this air purge further tends to remove any heavy hydrocarbon compounds which may have accumulated on the adsorbent bed. However, in many applications, this is unlikely since such will usually be captured by the process equipment of FIG. 1, and this air purge step may be omitted. If it is used, air is admitted only briefly to the first adsorbent bed 112, and the air admission is shut off by closing the valves 134 and 139. This momentary intrusion of air into the system will normally have a non-consequential effect on the product stream flowing through the product stream discharge conduit 166. If objectionable, the air admitted by the purge can be removed by simultaneously closing valve 167 and opening 170 to recycle the air via the recycle conduit 68 in the manner described above for the flushing hydrocarbon stream.

When the second adsorber 114 has been loaded with adsorbed hydrocarbon components from the incoming first product stream and regeneration is required, the regeneration cycle for the second adsorber 114 will be conducted in a manner described above for the regeneration cycle of the first adsorber 112. While the second adsorber 114 has been on-stream, the first adsorber 112 will have been regenerated and will be standing by awaiting to be placed in the onstream or adsorbing mode. At the end of the regeneration cycle for the first adsorber 112, the valve 142 will be closed and the liquid ring vacuum pump 150 will be deactivated. The second adsorber 114 will be taken off-stream by closing the valves 124 and 127 disposed in the second inlet conduit 120 and the second outlet conduit 128, respectively, and simultaneously, the first adsorber 112 will be put onstream by opening the valves 122 and 125 disposed in the first inlet conduit 118 and in the first outlet conduit 126, respectively. This routes the incoming first product stream of hydrocarbon-carrier gas mixture to the first adsorber 112 of the second adsorber battery 110 via the first inlet conduit 118.

Regeneration of the second adsorber 114 is commenced with the hydrocarbon flushing effected by opening valves 174 and 136 disposed in the product flushing conduit 172 and the flushing conduit 132, respectively, while opening valve 46 in the valve conduit 144 and actuating the liquid ring vacuum pump 150. With the exception that the aforestated apparatus are involved instead of that associated with the first adsorber 112, the regeneration, including the flushing by hydrocarbon rich gas, continues for the second adsorber 114 in the identical manner described above for the regeneration cycle of the first adsorber 112. Since the regeneration cycle will take less time than the time required to bring the on-stream adsorber to saturation, there will always be an off-stream adsorber waiting to be placed on-stream at the end of the process run for the on-stream adsorber. In this way, the first and second adsorbers 112, 114 of the second adsorber battery 110 alternate on-stream time.

It will be clear that the above described process as depicted in the flow layouts of FIGS. 1 and 2 is well suited to achieve the aforestated objects of the present invention. In practice, it has been determined that the process depicted in FIG. 1 is particularly suited to process hydrocarbon-carrier gas mixtures which have a hydrocarbon content above about 10% by volume. Hydrocarbon-carrier gas mixtures having less than about 10% by volume of hydrocarbon will usually be processed by the layout depicted in FIG. 2; in the case of the leaner inlet streams, the hydrocarbon enrichments provided by the flow layout of FIG. 2 will normally be required to assure continuous utilization of the discharged hydrocarbon product stream as a fuel. In a typical example of a lean gas input, the inlet vapor composition of 1% methane/99% air would produce a methane product of approximately 10% by volume methane and the flow layout of FIG. 1. The methane product from the flow layout of FIG. 1 would then be fed into the enrichment process depicted in FIG. 2 for an ultimate concentration of methane to approximately 90% by volume.

Although the above description has discussed a vacuum system, it will be understood that the pressure on the adsorbers during regeneration can be established at pressures at or above atmospheric pressure, since the change in pressure is the mechanism which effects the desorption of the adsorbent material. However, this desorption mechanism may be assisted by the use of temperature control of the bed in conjunction with, or to effect, the pressure reduction.

Figure 3:
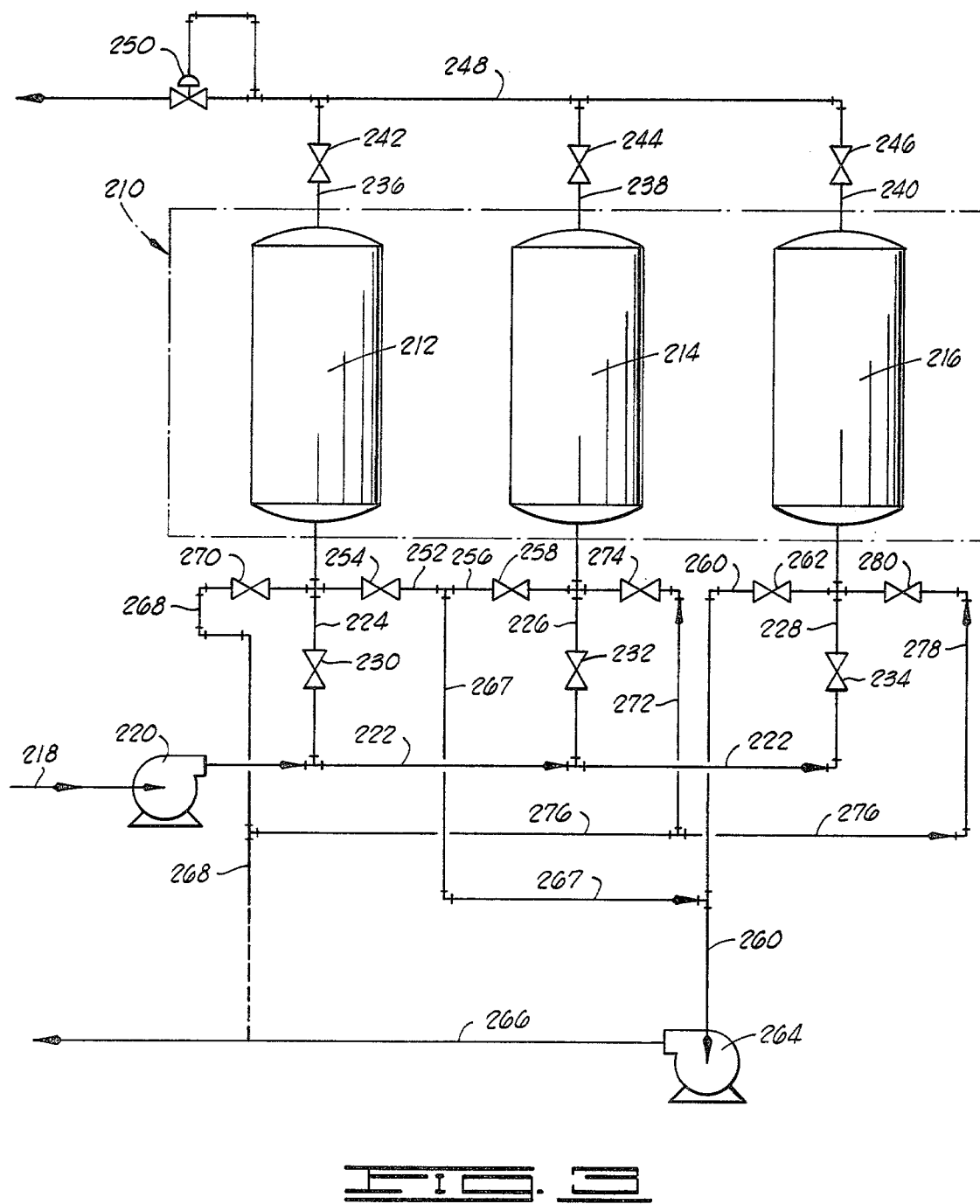
FIG. 3 is a flow diagram of another embodiment of the present invention.

The process depicted in FIG. 3 is another process flow layout constructed to practice the present invention, the flow layout of FIG. 3 being a pressurized system instead of the vacuum systems discussed above. An adsorber battery, depicted by the broken line box 210, comprises a first adsorber vessel 212, a second adsorber vessel 214, and a third adsorber vessel 216, each of the adsorber vessels 212, 214 and 216 containing a bed of solid adsorbent material such as that described for FIGS. 1 and 2. The adsorbers 212, 214 and 216 are each provided with internal adsorbent baffles or plates, gas flow directing baffles, and high pressure relief valves, as well as pressure and temperature indicating gauges conventionally employed with solid adsorbent devices; however, as above, the process layout depicted in FIG. 3 is simplified and these details are not shown.

A feed conduit 218 is connected to a source of hydrocarbon-carrier gas and is connected to the suction port of a compressor 220 which raises the pressure of the inlet feed stream and passes the pressurized feed stream to a feed conduit 222. The feed conduit 222 is connected to a first inlet conduit 224, to a second inlet conduit 226 and to a third inlet conduit 228 leading, respectively, to the first, second and third adsorbers 212, 214 and 216. Valves 230, 232 and 234 are provided in the first, second and third inlet conduits 224, 226 and 228 respectively.

A first outlet conduit 236, a second outlet conduit 238 and a third outlet conduit 240 are provided as exhaust or discharge lines for the first, second and third adsorbers 212, 214 and 216, respectively. The outlet conduits 236, 238 and 240 have valves 242, 244 and 246 disposed therein, respectively, and connect to a carrier gas outlet conduit 248 which leads to a venting discharge area such as to an atmospheric discharge discharge point, for example. Disposed in the carrier gas outlet conduit 248 is a pressure regulator 250 which controls the discharge pressure of the adsorber battery 210.

A first discharge conduit 252, having a valve 254 disposed therein, connects to the first inlet conduit 224 between the valve 230 and the first adsorber 212; a second discharge conduit 256, having a valve 258 disposed therein, connects to the second inlet conduit 226 between the valve 232 and the second adsorber 214; and a third discharge conduit 260, having a valve 262 disposed therein, connects to the third inlet conduit 228 between the valve 234 and the third adsorber 216. The third discharge conduit 260 connects to the suction port of a product and flushing gas compressor 264 which compresses the discharged gas flowing to it and passes the pressurized gas to a final discharge conduit 266. The first discharge conduit 252 and the second discharge conduit 256 connect to the conduit 267 which is connected to the third discharge conduit 260. Of course, if the enriched product gas is not required to be at elevated pressures, the product and flushing gas compressor 264 would not be provided.

A first product flushing conduit 268, having a valve 270 disposed therein, may interconnect with the final product discharge conduit 266 and with the first inlet conduit 224 between the valve 230 and the first adsorber 212, or the first product flushing conduit 268 may be connected to a source of hydrocarbon gas, such as methane, when processing the example methane-air mixtures discussed above. A second product flushing conduit 272, having a valve 274 disposed therein, connects to a flushing conduit 276, which is connected to the first product flushing conduit 268, and to the second inlet conduit 226 between the valve 232 and the second adsorber 214. A third product flushing conduit 278, having a valve 280 disposed therein, connects to the flushing conduit 276 and to the third inlet conduit 228 between the valve 234 and the third adsorber 216.

Having described the equipment depicted in the flow layout of FIG. 3, the discussion will now turn to an operative example. An inlet stream of hydrocarbon-carrier gas mixture is admitted to the feed-gas compressor 220 via the inlet feed conduit 218, and the compressed inlet stream is passed through the first adsorber 212 via the first inlet conduit 224, assuming the first adsorber 212 is on stream. In this profile, the valve 230 will be open as will the valve 242, but the other valves will be assumed closed unless specifically mentioned otherwise. Hydrocarbons are adsorbed in the first adsorber 212, and the carrier gas exits the system via the exhaust conduit 236 to the carrier gas outlet conduit 248, with the pressure regulator 250 operating to establish the discharge pressure. During the time that the inlet stream of hydrocarbon-carrier gas is flowing through the first adsorber 212, it will be assumed that the second adsorber 214 is undergoing regeneration, which will be conducted as follows. First, a flushing gas mixture is passed into the second adsorber 214 via the flushing conduits 276, 272 with the valve 274 open; this flushing gas mixture displaces the carrier gas out of the second adsorber 214 via the second outlet conduit 238 and the valve 244 (which is open). After a preset volume of flushing gas mixture is supplied to the second adsorber 214, valves 274 and 244, disposed in the flushing conduit 272 and the second outlet conduit 238, respectively, are closed. Next, valve 258 disposed in the second discharge conduit 256 is open, and the second adsorber 214 depressures to atmospheric pressure by flowing its hydrocarbon contents to the product and flushing gas compressor 264 via the conduits 267 and 260.

While the above described processes are occurring, the third adsorber 216 is being repressured following its regeneration cycle. This is accomplished by opening valve 234 while all of the other valves associated with the conduits connected to the third adsorber 216 remain closed. The inlet hydrocarbon-carrier gas mixture flows across the valve 234 until the third adsorber 216 reaches the same pressure as that contained in the feed conduit 222. Of course, the third adsorber 216 could also be repressured with carrier gas by opening only valve 246 in the third outlet conduit 240.

When the third adsorber 216 has reached the same pressure as in the first adsorber 212, all of the inlet mixture of hydrocarbon-carrier gas is directed through the third adsorber 216 by opening the valves 234 and 246 and closing the valve 230 in the first inlet conduit 224. The first adsorber 212 will then be flushed and regenerated at the same time that the second adsorber 214 is being repressured. In this manner, each of the adsorbers passes through the following cycle: (1) processing the inlet stream of hydrocarbon-carrier gas; (2) undergoing flushing and depressurization; and (3) repressuring.

Continuing with the operative example, the first adsorber 212 will be regenerated as follows. First, flushing gas is passed into the first adsorber 212 via the first product flushing conduit 268 by opening valve 270, which displaces carrier gas out of the first adsorber 212 via the first outlet conduit 236 and valve 242 (which is open). After a preset volume of flush gas is supplied to the first adsorber 212, valves 270 and 242 are closed. Valve 254 is then opened and the first adsorber 212 depressures to atmospheric pressure by flowing its hydrocarbon content to the product and flushing gas compressor 264 via the conduits 252, 267 and 260. Meanwhile, the second adsorber 214, which has undergone regeneration, is repressured by opening valve 232 in the second inlet conduit 226, and by leaving all other valves associated with conduits connected to the second adsorber 214 closed. The inlet stream of hydrocarbon-carrier gas mixture flows across valve 232 until the second adsorber 214 reaches the same pressure as contained in the feed conduit 222. (As mentioned above, an alternate method for repressuring the second adsorber 214 is to keep the valve 232 closed and open valve 244 to repressure with carrier gas from the carrier gas outlet conduit 248.) When the second adsorber 214 has reached the same pressure as that in the on-stream third adsorber 216, all of the inlet stream of hydrocarbon-carrier gas mixture is directed through the second adsorber 214 by closing valves 234 and 246 disposed in the third inlet conduit 228 and the third outlet conduit 240, respectively. At this point, the third adsorber 216, which has been onstream, is ready for regeneration.

The third adsorber 216 is regenerated in the manner described above for the other adsorbers; that is, flushing gas is passed into the third adsorber 216 by opening the valve 280 to permit the inlet stream of hydrocarbon-carrier gas mixture to push carrier gas out of the third adsorber 216 via the open valve 246 and the third outlet conduit 240. After a preset volume of flush gas is supplied to the third adsorber 216, valves 280 and 246 are closed. Valve 262 is then opened and the third adsorber 216 depressures to atmospheric pressure by flowing its hydrocarbon contents to the product and flush gas compressor 264 via the conduit 260. Meanwhile, the second adsorber 214 is on-stream, and the first adsorber 212 is repressured by opening valve 230 in the first inlet conduit 224. Inlet hydrocarbon-carrier gas flows across the valve 230 until the first adsorber 212 reaches the same pressure as that in the feed conduit 222. (As before, an alternate method to repressure the first adsorber 212 is to open the valve 242 and repressure with carrier gas from the carrier gas outlet conduit 248.)

The process layout of FIG. 3 provides for a forward flushing as opposed to the backflushing which is utilized in FIGS. 1 and 2. That is, flushing is accomplished by flowing substantially purified hydrocarbon gas into the bottom of the adsorbant vessels and regeneration is accomplished by reducing the pressure to atmospheric pressure. Of course, the flushing gas can be introduced at other points in the adsorbers, but it is believed that forward flushing as described in FIG. 3 is preferable for the practice of the present invention when utilizing higher pressures. The reason for this is that two phenomena occur during flushing. First, the carrier gas is forced out of the void space of adsorber vessels by displacement when flushing gas is introduced. Secondly, and apparently more importantly at elevated pressures, the adsorbent material adsorbs significant quantities of flushing gas and simultaneously releases adsorbed carrier gas. This phenomena becomes important at elevated pressures because the carrier gas is substantially adsorbed and would dilute the enriched product gas if it were not desorbed during flushing.

Thus it is clear that the present invention is well adapted to carry out the objects and attain the ends and advantages mentioned as well as those inherent therein. While a presently preferred embodiment of the invention has been described for purposes of this disclosure, it will be understood that numerous changes may be made which will readily suggest themselves to those skilled in the art and which are accomplished within the spirit of the invention disclosed and as defined in the appended claims.

What is claimed is:

1. A process for recovering hydrocarbon components from a hydrocarbon-carrier gas mixture, comprising:

passing an inlet stream of the hydrocarbon-carrier gas mixture through a first adsorber containing an adsorbent material capable of selectively adsorbing the hydrocarbon components from the mixture and simultaneously venting a first venting stream of substantially hydrocarbon free carrier gas therefrom, while maintaining the pressure on the adsorbent material at substantially that of the inlet stream;

terminating the flow of the inlet stream to the first adsorber;

flushing the adsorbent material of the first adsorber with a flushing stream of gas which will be adsorbed to a greater degree than the carrier gas so that the carrier gas is displaced from the adsorbent bed to produce a displaced carrier gas stream; and venting the displaced carrier gas stream from the first adsorber; and lowering the pressure of the hydrocarbon laden adsorbent material of the first adsorber to desorb the hydrocarbon components therefrom and producing thereby a first product stream comprising a gas mixture rich in the adsorbed hydrocarbon components.

2. The process of claim 1 wherein the flushing stream is a mixture rich in the adsorbed hydrocarbon components.

3. The process of claim 1 wherein the carrier gas is substantially comprised of air.

4. The process of claim 3 wherein the inlet stream is substantially comprised of air and methane.

5. The process of claim 1 wherein the flushing stream is a portion of the first product stream.

6. The process of claim 1 further comprising the step of passing a quantity of stripping gas into contact with the adsorbent material of the first adsorber when the pressure has been lowered.

7. The process of claim 6 wherein the stripping gas is air.

8. The process of claim 1 further comprising the step of:
passing the inlet stream, immediately following termination of flow to the first adsorber, through a second adsorber containing an adsorbent material capable of selectively adsorbing the hydrocarbon components from the hydrocarbon-carrier gas mixture and simultaneously venting a continuation of the first venting stream of substantially hydrocarbon free carrier gas, while maintaining the adsorbent material at substantially the pressure of the inlet stream.

9. The process of claim 8 further comprising the step of:
combining the vented displaced carrier gas stream from the first adsorber with the inlet stream so that the displaced carrier gas stream is recycled through the second adsorber when the inlet stream is passed therethrough.

10. The process of claim 9 wherein the step of lowering the pressure of the first adsorber comprises subjecting the hydrocarbon laden adsorbent material of the first adsorber to a vacuum.

11. The process of claim 10 wherein the step of lowering the pressure of the first adsorber to a vacuum comprises:
subjecting the hydrocarbon laden adsorbent material of the first adsorber to a liquid ring vacuum pump to produce the first product stream containing a liquid from the liquid ring vacuum pump; and
separating the hydrocarbon components comprising the first product stream from the liquid injected into the first product stream by the liquid ring vacuum pump.

12. The process of claim 8 further comprising the steps of:
terminating the flow of the inlet stream to the second adsorber;
flushing the adsorbent material of the second adsorber with a flushing stream of gas which will be adsorbed to a greater degree than the carrier gas so that the carrier gas is displaced from the adsorbent material to produce a displaced carrier gas stream and venting the displaced carrier gas stream therefrom; and
lowering the pressure of the hydrocarbon laden adsorbent material of the second adsorber to desorb the hydrocarbon components therefrom and producing thereby a further amount of the first product stream comprising a gas mixture rich in the adsorbed hydrocarbon components.

13. The process of claim 12 wherein the flushing stream is a mixture rich in the adsorbed hydrocarbon components.

14. The process of claim 12 wherein the carrier gas is substantially comprised of air.

15. The process of claim 13 wherein the inlet stream is substantially comprised of air and methane.

16. The process of claim 12 wherein the flushing stream to the second adsorber is a portion of the first product stream.

17. The process of claim 16 further comprising the step of passing a quantity of stripping gas into contact with the adsorbent material of the first and second adsorbers when the pressure has been lowered on the respective bed.

18. The process of claim 17 wherein the stripping gas is air.

19. The process of claim 12 further comprising the steps of:
terminating the lowering of pressure of the first adsorber;
passing the inlet stream immediately following termination of flow to the second adsorber, through the first adsorber; and
combining the vented displaced carrier gas stream from the second adsorber with the inlet stream so that the displaced carrier gas stream from the second adsorber is recycled through the first adsorber when the inlet gas is passing through the first adsorber.

20. The process of claim 12 wherein the step of lowering the pressure of the second adsorber comprises subjecting the hydrocarbon laden adsorbent material of the second adsorber to a vacuum.

21. The process of claim 20 wherein the step of lowering the pressure of the second adsorber to a vacuum comprises:
subjecting the hydrocarbon laden adsorbent material of the second adsorber to a liquid ring vacuum pump to produce the further amount of first product stream containing a liquid from the liquid ring vacuum pump;
separating the hydrocarbon components comprising the first product from the liquid injected into the first product stream by the liquid ring vacuum pump.

22. The process of claim 20 wherein the carrier gas is substantially comprised of air.

23. The process of claim 21 wherein the carrier gas is substantially comprised of air.

24. The process of claim 22 wherein the inlet stream is substantially comprised of air and methane.

25. The process of claim 23 wherein the inlet stream is substantially comprised of air and methane.

26. The process of claim 1 wherein the first adsorber is designated as a portion of a first adsorber battery, and the process further comprises the steps of:
passing the first product stream through a first adsorber of a second adsorber battery, the first adsorber of the second adsorber battery containing an adsorbent material capable of selectively adsorbing the hydrocarbon components from the first product stream and simultaneously venting a second venting stream of substantially hydrocarbon free carrier gas therefrom, while maintaining the pressure on the adsorbent material at substantially that of the first product stream;
terminating the flow of the first product stream to the first adsorber of the second adsorber battery;
flushing the adsorbent material of the first adsorber of the second adsorber battery with a flushing stream of gas which will be adsorbed to a greater degree than the carrier gas so that the carrier gas is displaced from the adsorbent bed to produce a displaced carrier gas stream and venting the displaced carrier gas stream therefrom; and
lowering the pressure of the hydrocarbon laden adsorber material of the first adsorber of the second adsorber battery to desorb the hydrocarbon components therefrom and producing thereby a second product stream comprising a gas mixture rich in the adsorbed hydrocarbon components.

27. The process of claim 26 wherein the flushing stream is a mixture rich in the adsorbed hydrocarbon components.

28. The process of claim 26 wherein the carrier gas is substantially comprised of air.

29. The process of claim 28 wherein the inlet gas is substantially comprised of air and methane.

30. The process of claim 26 wherein the flushing streams are portions of a selected one of the first and second product streams.

31. The process of claim 26 further comprising the step of passing a quantity of stripping gas into contact with the adsorbent material of the first adsorber of the second adsorber battery when the pressure has been lowered.

32. The process of claim 31 wherein the stripping gas is air.

33. The process of claim 26 further comprising the step of:
passing the first product stream, immediately following termination of flow to the first adsorber of the second adsorber battery, through a second adsorber of the second adsorber battery containing an adsorbent material capable of selectively adsorbing the hydrocarbon components from the first product stream and simultaneously venting a continuation of the second venting stream of substantially hydrocarbon-free carrier gas, while maintaining the adsorbent material of the second adsorber substantially at the pressure of the first product stream.

34. The process of claim 33 comprising the step of:
combining the vented displaced carrier gas from the first adsorber of the second adsorber battery with the first product stream so that the vented displaced carrier gas stream is recycled through the second adsorber of the second adsorber battery when the first product stream is passed therethrough.

35. The process of claim 34 wherein the step of lowering the pressure of the first adsorber comprises subjecting the hydrocarbon laden adsorbent material of the first adsorber of the second battery to a vacuum.

36. The process of claim 35 wherein the step of lowering the pressure of the hydrocarbon laden material of the first adsorber of the second adsorber battery to a vacuum comprises:
subjecting the hydrocarbon laden adsorbent material of the first adsorber of the second adsorber battery to a liquid ring vacuum pump to produce the second product stream containing a liquid from the liquid ring vacuum pump; and
separating the hydrocarbon components comprising the second product stream from the liquid injected into the second product stream by the liquid ring vacuum pump.

37. The process of claim 33 further comprising the steps of:
terminating the flow of the first product stream to the second adsorber of the second adsorber battery;
flushing the adsorbent material of the second adsorber of the second adsorber battery with a flushing stream of gas which will be adsorbed to a greater degree than the carrier gas so that the carrier gas is displaced from the adsorbent material to produce a displaced carrier gas stream and venting the displaced carrier gas stream therefrom;
lowering the pressure of the hydrocarbon laden adsorbent material of the second adsorber of the second adsorber battery to desorb the hydrocarbon components therefrom and producing thereby a further amount of the second product stream comprising a gas mixture rich in the adsorbed hydrocarbon components.

38. The process of claim 37 wherein the flushing stream is a mixture rich in the adsorbed hydrocarbon components.

39. The process of claim 37 wherein the carrier gas is substantially comprised of air.

40. The process of claim 39 wherein the inlet stream is substantially comprised of air and methane.

41. The process of claim 37 wherein the flushing streams are portions of a selected one of the first and second product streams.

42. The process of claim 37 further comprising the step of passing a quantity of stripping gas into contact with the adsorbent beds of the adsorbers when the pressure has been lowered on the respective beds.

43. The process of claim 42 wherein the stripping gas is air.

44. A process for recovering hydrocarbons from an inlet stream of a hydrocarbon-carrier gas mixture comprising the steps of:
passing an amount of the inlet stream into contact with a solid adsorbent material so that the hydrocarbon is selectively adsorbed and a first venting stream of substantially hydrocarbon free air is simultaneously exhausted, while the adsorbent material is maintained at substantially the pressure of the inlet stream;
passing a flushing stream of rich hydrocarbon-carrier gas into contact with the solid adsorbent material;
desorbing the hydrocarbon from the solid adsorbent material to produce a rich hydrocarbon-carrier gas product stream;
passing the rich hydrocarbon-carrier gas product stream into contact with a further amount of the solid adsorbent material so that the hydrocarbon is selectively adsorbed and a second venting stream of substantially hydrocarbon free carrier gas is simultaneously exhausted, while the adsorbent material is maintained at substantially the pressure of the inlet stream;
passing another flushing stream of rich hydrocarbon-carrier gas into contact with the solid adsorbent material; and
desorbing the hydrocarbon from the further amount of solid adsorbent material to produce a richer hydrocarbon-air product stream.

45. The process of claim 44 in which the step of desorbing the hydrocarbon from the solid adsorbent material comprises subjecting the hydrocarbon laden adsorbent material to a vacuum with a liquid ring vacuum pump to produce a hydrocarbon vapor mixture containing a liquid from the liquid ring vacuum pump and recovered hydrocarbon, and further comprosing the step of:
separating the hydrocarbon from the liquid injected into the desorbed vapor by the liquid ring vacuum pump.

46. The process of claim 44 in which the steps of desorbing the hydrocarbon from the solid adsorbent material comprises subjecting the adsorbent material comprises subjecting the adsorbent material to a vacuum liquid ring vacuum pumps to produce in each step a hydrocarbon vapor mixture containing a liquid from the respective liquid ring vacuum pump and recovered hydrocarbon, and further comprising the step of:

separating the hydrocarbon from the liquid injected into the desorbed vapor by the liquid ring vacuum pump.

47. A process for recovering hydrocarbon from a hydrocarbon-air mixture, comprising the steps of:
   (a) passing the hydrocarbon-air mixture through an adsorber having a solid adsorbent bed capable of selectively adsorbing hydrocarbon components from the mixture to leave substantially hydrocarbon free air;
   (b) simultaneously venting the substantially hydrocarbon free air to the atmosphere, while maintaining the adsorbent bed at substantially the pressure of the hydrocarbon-air mixture;
   (c) flushing the solid adsorbent bed with a flushing stream of gas which will be adsorbed to a greater degree than the carrier gas so that the carrier gas is displaced from the adsorbent bed and venting a displaced carrier gas therefrom;
   (d) submitting the hydrocarbon laden solid adsorbent bed to a vacuum with a first liquid ring vacuum pump to desorb the hydrocarbon components therefrom and produce a rich hydrocarbon-air vapor mixture containing a liquid from the first liquid ring vacuum pump and recovered hydrocarbon from the mixture;
   (e) separating the hydrocarbon and the liquid injected in the vapor by the liquid ring vacuum pump to produce a first product stream comprising a gas mixture rich in the adsorbed hydrocarbon components;
   (f) passing the first product stream to another adsorber having a solid adsorbent bed capable of selectively adsorbing the hydrocarbon components from the first product stream to leave substantially hydrocarbon free air;
   (g) simultaneously venting the substantially hydrocarbon free air to the atmosphere, while maintaining the adsorbent bed at substantially the pressure of the first product stream;
   (h) flushing the other solid adsorbent bed with a flushing stream of gas which will be adsorbed to a greater degree than the carrier gas so that the carrier gas is displaced from the adsorbent bed and venting a further amount of the displaced carrier gas;
   (i) submitting the other hydrocarbon laden solid adsorbent bed to a vacuum with a liquid ring vacuum pump to desorb the hydrocarbon components therefrom and produce a rich hydrocarbon-air vapor mixture containing a liquid from the second liquid ring vacuum pump and recovered hydrocarbon from the first product stream; and
   (j) separating the hydrocarbon and the liquid injected in the vapor by the second liquid ring vacuum pump to produce a second product stream comprising a gas mixture richer in the adsorbed hydrocarbon components.

48. The process of claim 47 wherein the liquid ring vacuum pump liquid is water.

49. The process of claim 47 wherein the liquid ring vacuum pump liquid is water mixed with an antifreeze material.

50. The process of claim 47 further comprising the step of admitting a quantity of air to the adsorber near the end of the vacuum step.

51. The process of claim 47 further comprising the step of:
    passing the displaced carrier gas from the first and second adsorbers through a selected on-stream one of the first and second adsorbers to produce a further quantity of substantially hydrocarbon free air.

* * * * *